(12) United States Patent
Loifenfeld et al.

(10) Patent No.: US 7,758,849 B2
(45) Date of Patent: Jul. 20, 2010

(54) HAIR WAX PRODUCTS CONTAINING SILICONE WAX, SILICONE-FREE WAX AND OILS

(75) Inventors: Marina Loifenfeld, Frankfurt am Main (DE); Bernd Stein, Hoesbach (DE); Michael Franzke, Rossdorf (DE)

(73) Assignee: Wella AG, Darmstadt (DE)

( * ) Notice: Subject to any disclaimer, the term of this patent is extended or adjusted under 35 U.S.C. 154(b) by 1427 days.

(21) Appl. No.: 11/042,231

(22) Filed: Jan. 25, 2005

(65) Prior Publication Data
US 2005/0163738 A1 Jul. 28, 2005

(30) Foreign Application Priority Data
Jan. 28, 2004 (DE) .................. 10 2004 004 155

(51) Int. Cl.
*A61K 8/00* (2006.01)
(52) U.S. Cl. .................. 424/70.1; 424/400
(58) Field of Classification Search .......... None
See application file for complete search history.

(56) References Cited

U.S. PATENT DOCUMENTS

| 5,690,924 | A | 11/1997 | Keil et al. |
| 5,885,561 | A * | 3/1999 | Flemming et al. ......... 424/62 |
| 6,503,944 | B1 * | 1/2003 | Chanchani .............. 514/506 |
| 6,582,679 | B2 | 6/2003 | Stein et al. |
| 2002/0122811 | A1 | 9/2002 | Stein et al. |
| 2003/0007943 | A1 | 1/2003 | Krause et al. |
| 2003/0211070 | A1 | 11/2003 | Stein et al. |

FOREIGN PATENT DOCUMENTS

| DE | 1 617 421 | | 2/1972 |
| EP | 0 760 235 | A1 | 3/1997 |
| EP | 0 868 898 | A1 | 7/1998 |
| EP | 1 197 201 | A2 | 4/2002 |
| EP | 1 266 650 | A1 | 12/2002 |

OTHER PUBLICATIONS

"International Cosmetic Ingredient Dictionary and Handbook", 9-th Edition, 2002, pp. 2920-2921.

* cited by examiner

*Primary Examiner*—Eric E. Silverman
(74) *Attorney, Agent, or Firm*—Michael J. Striker

(57) ABSTRACT

The solid hair wax product for treating or setting up a human hair-do or hair style contains at least one silicone-free wax, at least one hydrophobic oil that is liquid at 25° C. and at least one silicone wax with a melting point in a range of from 20 to 45° C. Preferably the silicone-free wax is a hydrocarbon wax, the hydrophobic oil is a silicone oil and the silicone wax is an alkylmethyl-dimethyl-siloxane.

13 Claims, No Drawings

HAIR WAX PRODUCTS CONTAINING SILICONE WAX, SILICONE-FREE WAX AND OILS

BACKGROUND OF THE INVENTION

1. Field of the Invention

The subject matter of the present invention is a wax product for treatment of or setting up a human hairstyle. The wax product of the present invention comprises a composition containing a silicone wax with a melting point near the temperature of the human body, oil that is a liquid at room temperature and a silicone-free wax that is solid at room temperature.

2. Related Art

Styling wax compositions are known products for hair treatment. They find application particularly in putting short to medium length hair in a fashionable hairstyle and impart hold and luster as well as stabilize, condition and fix the hairstyle. Also a hair-do may be shaped and provided with texture with a hair wax. Conventional hair waxes are usually provided in cups or other vessels and their action is based on the following principle: Product is removed with the fingers. The wax is distributed on the surface of the hand and then melted or at least considerably softened by the heat of the hand. It is possible to work the otherwise too hard wax into the hair because of this softening or melting. The wax is worked into the hair in a softened or more or less liquid state. Then it cools and again reaches its original consistency. It hardens and the hairdo obtained has stability and hold and frequently a slightly wet look. Conventional hair wax products, as they are currently marketed, are usually based on hydrophobic, non-silicone containing waxes, fats and oils. They contain a large amount of hydrophobic materials, such as plant or animal waxes, fatty acid esters, fatty alcohols, etc. The main ingredients and primary effective ingredients are hydrophobic waxes, such as e.g. ozocerite, candelilla wax, bees wax, caranauba wax, etc. These types of products have the disadvantage that they have a comparatively high undesirable stickiness besides the desired effects when they are applied to the hair.

SUMMARY OF THE INVENTION

It is an object of the present invention to provide a solid hair wax product for treating hair, which melts or softens to a fluid or softened consistency and has as little stickiness as possible or preferably no stickiness when rubbed by hand.

It is another object of the present invention to provide a solid hair wax product for treating hair, which provides the hair with a natural look and movability after application to the hair and, in preferred embodiments, can be used to tint individual hair strands or locks.

It is also an object of the present invention to provide a solid hair wax product for treating hair, which is easily removed from its package, easily worked or processed and which has good application properties, and which especially is satisfactory worked into the hair, has good distributability in the hair, good hair-style definition and provides luster and hold, and fixes and stabilizes a hair-do.

It has been found that the objects of the present invention are attained by a solid hair wax product for treating or setting up a human hair-do or hair style, which contains a silicone wax with a melting point near the temperature of the human body, an oil compound that is a liquid at room temperature and a silicone-free wax that is solid at room temperature.

According to the invention the hair wax product with a solid, wax-like or waxy consistency for treating or setting up a human hair-do or hair style contains
(A) at least one silicone-free wax;
(B) at least one hydrophobic oil compound which is liquid at 25° C.; and
(C) at least one silicone wax with a melting point in a range of from 20° C. to 45° C.

The waxy consistency is characterized by a needle penetration number (measurement unit, 0.1 mm, test weight including guide rod 25 g, test duration 5 s, test temperature of 25° C., Geometry of the hollow cone according to DIN 51 580), preferably greater than or equal to 10, especially from 10 to 60, from 15 to 55 or from 25 to 50. The product has a solidification point, which is greater than or equal to 30° C. and especially in a preferred range from 40° C. to 55° C.

Silicone-Free Waxes

The silicone-free wax is present in the solid hair wax product preferably in an amount of from 10 to 40 percent by weight, especially from 15 to 30 or from 15 to 25 percent by weight. It has a solidification point of preferably about 40° C. or above 55° C. The needle penetration number is preferably in a range of from 2 to 70, especially of from 3 to 40. Preferably the hair wax product contains at least one wax, which has a needle penetration point of les than 40, especially preferably less than 20.

Suitable silicone-free waxes include, e.g., animal wax, vegetable wax, mineral wax, synthetic wax, microcrystalline wax, macrocrystalline wax, paraffin wax, ozokerite, montan wax, Fischer-Tropsch wax, polyolefin wax (such as polyethylene, polybutene and the like wax), beeswax, lanolin and its derivatives e.g. lanolin alcohol, candelilla wax, caranauba wax, Japan wax, hardened fat, fatty acid esters and/or fatty acid glycerides. A preferred embodiment contains hydrocarbon wax, e.g. ozokerite or ceresin, as the silicone-free wax, especially with a needle penetration number of less than 20.

Liquid, Hydrophobic Oils

The liquid hydrophobic oils are preferably contained in an amount of from 20 to 80 percent by weight, especially preferably from 30 to 70 or 40 to 55 percent by weight. They have a melting point of less than or equal to 25° C. and a boiling point over 250° C., preferably over 300° C. Generally oils known to those skilled in the art can be used as the hydrophobic oil. Preferably these oils are silicone compounds. Suitable silicone oils are e.g. linear polydimethyl-siloxanes (dimethicone), cyclic polydimethylsiloxanes (cyclomethicone), hydroxy-substituted polydimethylsiloxanes (diemthiconols), amino-substituted silicones (e.g. amodimethicone) and siloxanes substituted with aromatic groups (e.g. phenylated silicones, polyphenylmethylsioxanes, phenyltrimethicone).

Additionally or alternatively also hydrophobic, silicone-free oils can be used. These oils include vegetable or animal oils, mineral oils (Paraffinium liquidum) or their mixtures. Furthermore the following hydrocarbon oils are also suitable: hydrocarbon oils, such as paraffin or isoparaffin oils, squalane, oils from fatty acids and polyols, especially triglycerides. Suitable vegetable oils include e.g. sunflower seed oils, coconut oil, castor oil, lanolin oils, jojoba oil, corn oil and soy oil.

Silicone Waxes

The silicone waxes are preferably employed in an amount of from 5 to 40 percent by weight, especially from 10 to 25 or from 10 to 20 percent by weight. They have a melting point in a range of from 20° C. to 45° C., preferably in a range of from 20° C. to 40° C. or up to 35° C.

The silicone waxes are preferably alkyl-methyl-dimethyl-siloxanes, especially those in which the alkyl group has at least 8 carbon atoms, e.g. 16 to 20 carbon atoms. Alkylmethyl-dimethylsiloxanes have the generally formula:

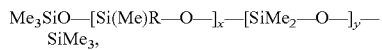

wherein Me is a methyl group and R is an alkyl group with preferably 8 to 22 carbon atoms and x and y are numbers greater than 0.

A preferred embodiment of the hair wax product of the invention contains the stearylmethyl-dimethylsiloxane (INCI: Stearyl dimethicone). Commercial products include e.g. Abil Wax 9800, DC 2503 Wax, SilCare 41 M65, Silsoft W-18 and Belsil SDM 5055.

Emulsifiers

Preferred embodiments of the hair wax product of the invention include at least one emulsifier. The emulsifiers are preferably contained in an amount of from 0.1 to 30 percent by weight, from 0.5 to 25 percent by weight, or from 3 to 20 percent by weight. The emulsifiers can be non-ionic, anionic, cationic, amphoteric or zwitterionic. Non-ionic surfactants are preferred as the emulsifiers. Suitable non-ionic surfactants include, e.g.:

ethoxylated products of fatty alcohols, of fatty acids, of fatty acid glycerides or of alkylphenols, especially addition products of 2 to 30 mol ethylene oxide and/or 1 to 5 mol propylene oxide to $C_8$- to $C_{22}$-fatty alcohols, to $C_{12}$- to $C_{22}$-fatty acids or to alkylphenols with 8 to 15 carbon atoms in their alkyl groups;

$C_{12}$- to $C_{22}$-fatty acid monoesters and diesters of addition products of 1 to 30 mol ethylene oxide with glycerol;

addition products of 5 to 60 mol of ethylene oxide with castor oil or hardened (hydrogenated) castor oil; and monoesters, diesters and/or triesters of phosphoric acid with addition products of 2 to 30 mol of ethylene oxide with $C_8$- to $C_{22}$-fatty alcohols;

fatty acid sugar esters, especially esters of saccharoses and one or two fatty acids with 8 to 22 carbon atoms; e.g. compounds with the INCI names: sugar cocoate, sucrose dilaurate, sucrose distearate, sucrose laurate, sucrose myristate, sucrose oleate, sucrose palmitate, sucrose ricinoleate, sucrose stearate;

ethoxylated sorbitan fatty acid esters, especially esters of sorbitan and one, two or three fatty acids with 8 to 22 carbon atoms and with an ethoxylation degree of 4 to 20, for example compounds with the INCI names, polysorbate x, wherein x is the ethoxylation degree; and polyglyceryl fatty acid esters, especially of one, two or several fatty acids with 8 to 22 carbon atoms and polyglycerol with preferably 2 to 20 glyceryl units.

The emulsifiers can have a liquid or solid consistency at room temperature. In a particularly preferred embodiment the emulsifiers have a wax-like consistency and a liquifying point over 25° C.

Hair-Fixing Polymers

In a preferred embodiment the hair wax product according to the invention contains at least one hair-fixing polymer. The hair-fixing polymers are preferably contained in an amount of from 0 to 15 percent by weight, 0.1 to 10 percent by weight or 0.5 to 5 percent by weight.

Suitable hair-fixing polymers especially are the polymers described in "International Cosmetic Ingredient Dictionary and Handbook, $9^{th}$ Edition, pp. 2920 to 2921, under polymers the function "Hair Fixatives".

The hair-fixing polymers can be anionic, cationic, zwitterionic, nonionic and amphoteric polymers. They can be natural or synthetic polymers. The term "synthetic polymer" means a polymer, which is purely synthetic, or not of natural origin, especially those polymers, which are made by radical polymerization of ethylenically unsaturated monomers or by polycondensation. The term "natural polymer" means a polymer of natural origin, which can be understood as a polymer of natural origin, which also can be subsequently chemically or physically modified. Those polymers are preferred, which have sufficient solubility or dispersibility in a carrier medium, especially in water, alcohol and/or water/alcohol mixture, in order to be present in dissolved or uniformly dispersed form in the carrier medium. The term "hair-fixing polymer" means a polymer, which are in a position to deposit a polymer film on the hair and fix the hair when used in a 0.01 to 5 percent by weight aqueous, alcoholic or aqueous-alcoholic solution or dispersion.

Suitable nonionic polymers include homo-polymers or copolymers, which are built up from at least one of the following monomers: vinyl lactams, especially vinyl pyrrolidone and vinyl caprolactam, vinyl esters, such as vinyl acetate, vinyl alcohols, acrylamides, methacrylamides, alkylacrylamides, dialkylacrylamides, alkylmethacrylamides, dialkylmethacrylamides, dialkylaminoalkylmethacrylamides, dialkylaminoalkylacrylamides, alkylacrylates, alkylmethacrylates, propylene glycol or ethylene glycol, wherein the alkyl groups of these monomers preferably are $C_1$- to $C_7$-alkyl groups, especially preferably $C_1$- to $C_3$-alkyl groups. For example, homopolymers of vinyl caprolactams, of vinyl pyrrolidone or of N-vinylformamide are suitable. Further suitable synthetic film-forming, non-ionic hair-fixing polymers are, e.g., copolymerizates of vinyl pyrrolidone and vinyl acetate, terpolymers of vinyl pyrrolidone, vinyl acetate and vinyl propionate, polyacrylamides, polyvinyl alcohols and polyethylene glycol/polypropylene glycol copolymers. Polyvinyl pyrrolidone, polyvinyl caprolactam and their copolymers with at least one further nonionic monomer, especially polyvinylpyrrolidone/vinyl acetate copolymers, are especially preferred.

Suitable anionic hair-fixing polymers include synthetic homo- or copolymers with neutralizable monomer units containing acid groups, which are copolymerizable with comonomers, if necessary, which contain no acid groups. The acid groups may include —COOH, —$SO_3H$, —$OSO_3H$, —$OPO_2H$, —$OPO_3H_2$, of which carboxylic acid groups are particularly preferred. The acid groups can be unneutralized, or partially or completely neutralized. Preferably they present in 50 to 100% anionic or neutralized form. Organic or inorganic bases suitable for cosmetic purposes can be used as neutralization agents. For example, suitable bases include aminoalcohols, such as aminomethylpropanol (AMP), triethanolamine, monoethanolamine or tetrahydroxypropylethyleneamine and ammonia, NaOH and others. Suitable monomers include unsaturated, radical polymerizable compounds, which have at least one acid group, especially carboxyvinyl monomers. Suitable monomers containing acid groups include e.g. acrylic acid, methacrylic acid, crotonic acid, maleic acid or maleic acid anhydride or their monoesters.

The comonomers not substituted with acid groups include, e.g., acryl amide, methacrylamide, alkyl and dialkylacrylamides, alkyl and dialkylmethacrylamides, alkylacrylates, alkylmethacrylates, vinyl caprolactone, vinyl pyrrolidone, vinyl esters, vinyl alcohol, propylene glycol or ethylene glycol, amine-substituted vinyl monomers, such as dialkylaminoalkylacrylates, dialkylaminoalkylmethacrylates, monoalkylaminoalkylacrylates and monoalkylaminoalkylmethacrylates, in which the alkyl groups of these monomers are preferably alkyl $C_1$- to $C_7$-groups, especially preferably $C_1$- to $C_3$-alkyl groups.

Suitable anionic polymers include especially copolymers of acrylic acid or methacrylic acid with monomers selected from the group consisting of acrylic acid or methacrylic acid esters, acryl amides, methacrylamides and vinyl pyrrolidones, homopolymers of crotonic acid and copolymers of crotonic acid with monomers selected from the group consisting of vinyl esters, acrylic acid esters, methacrylic acid esters, acrylamides and methacrylamides. A suitable natural polymer is, for example, shellac. Preferred polymers include cross-linked or uncross-linked vinyl acetate/crotonic acid copolymers. Preferred anionic polymers also include partially esterified copolymers of vinyl methyl ether and maleic acid anhydride. Other preferred anionic polymers include, for example, terpolymers of acrylic acid, alkyl acrylate and N-alkylacrylamide, especially acrylic acid/ethyl acrylate/N-t-butylacrylamide terpolymer or terpolymers of vinyl acetate, crotonate and vinyl alkanoate, especially vinyl acetate/crotonate/vinyl neodecanoate copolymers; copolymers of acrylic or methacrylic acid and acrylic or methacrylic acid alkyl esters, in which the alkyl roups preferably contain 1 to 7 C atoms, and polystyrene sulfonate.

Suitable hair-fixing amphoteric or zwitterionic polymersare polymers, which contain basic or cationic groups, especially primary, secondary, teriary or quaternary amine groups, besides acid or anionic groups. Zwitterionic polymers are polymers, which are built up from at least one type of monomer, which has both quaternary amine groups and also acid groups or are polymers, which are built up from at least one first type of monomer having quaternary amine groups and at least one second type of monomer having acid groups. Amphoteric polymers are, e.g., built up from at least one type of monomer, which has acid groups and at least one additional type of monomer, which has basic amine groups. For example amphoteric polymers can be copolymers formed from alkylacrylamides (especially octylacryl amide), alkylaminoalkylmethacrylate (especially t-butylaminoethylmethacrylate) and two or more monomers, namely acrylic acid, methacrylic acid or their $C_1$- to $C_4$-alkylesters. At least one type of monomer contains an acid group, such as the monomers which are marketed under the trademark AMPHOMER® or AMPHOMER® LV-71.

Further suitable polymers are copolymers of acrylic acid, methacrylate and methacrylamideopropyltrimethylammonium chloride (INCI: polyquaternium-47), copolymers made from acrylamidopropyltrimonium chloride and acrylates or copolymers made from acrylamide, acrylamidopropyltrimonium chloride, 2-amidopropylacrylamide sulfonate and DMAPA (INCI: Polyquaternium-43). Polymers with monomers carrying betaine groups are also suitable, such as copolymers of methacryloylethyl betaine and two or more monomers of acrylic acid or its simple esters, INCI name: Methacryloyl ethyl betaine/acrylates copolymer.

Suitable cationic polymers preferably contain quaternary amine groups. The cationic polymers can be homo-polymers or copolymers, in which the quaternary nitrogen groups are either part of the polymer chain or preferably substituents on one or more of the monomers. The monomers containing the ammonium or amino groups can be copolymerized with non-cationic monomers. Suitable cationic monomers include unsaturated, radically polymerizable compounds, which carry at least one cationic or basic group, especially ammonium-substituted vinyl monomers, such as trialkylmethacryloxyalkyl ammonium groups, trialkylacryloxyalkyl ammonium groups, dialkyldiallyammonium groups and quaternary vinyl ammonium monomer groups with cyclic, cationic nitrogen-containing groups, such as pyridinium imidazolium or quaternary pyrrolidones, e.g. alkylvinylimidizolium, alkylvinylpyridinium or alkylvinylpyrrolidone salts. The alkyl groups of these monomers are preferably lower alkyl groups, such as alkyl groups having one to seven carbon atoms, especially preferably from one to three carbon atoms. The monomers containing ammonium or amine groups cannot be copolymerized with non-cationic monomers. Acrylamides, methacrylamides, alkyl- and dialkylacrylamides, alkyl- and dialkylmethacrylamides, alkylacrylates, alkylmethacrylates, vinyl caprolactones, vinyl caprolactams, vinyl pyrrolidones, vinyl esters, such as vinyl acetate, vinyl alcohol, propylene glycol or ethylene glycol are especially suitable as comonomers. Comonomers in which the alkyl groups have one to seven carbon atoms, especially one to three carbon atoms, are particularly preferred.

Suitable cationic polymers with quaternary amine groups are, for example, the polymers described with the trade name Polyquaternium in the CTFA Cosmetic Ingredient Dictionary, such as methylvinylimidazolium chloride/vinylpyrrolidone copolymer (Polyquaternium-16) or quaternized vinyl pyrrolidone/dimethylaminoethyl-methacrylate copolymer (Polyquaternium-11) and quaternary silicone polymers or oligomers, such as silicone polymers with quaternary terminal groups (Quaternium-80). For example, vinyl pyrrolidone/dimethylaminoethylmethacrylate methosulfate copolymer, sold under the trademark GAFQUAT® 755 N and GAFQUAT® 734 of GAF Co., USA, are suitable as a cationic polymer in the composition according to the invention. Other cationic polymers which are suitable include, for example, the copolymer of polyvinyl pyrrolidone and imidazoliminemethochloride under the trade name LUVIQUAT® HM 550 sold by BASF, Germany; the terpolymer of dimethyldiallylammonium chloride, sodium acrylate and acrylamide sold by Calgon, USA under the trade name MERQUAT® Plus 3300; the terpolymer of vinyl pyrrolidone, dimethylaminoethylmethacrylate and vinyl caprolactam sold under the trademark GAFFIX® VC 713 of ISP, USA; the vinyl pyrrolidone/methacrylamidopropyltrimethyl ammonium chloride copolymer sold under the trademark GAFQUAT® HS 100.

Suitable cationic polymers, which are derived from natural polymers, are cationic derivatives of cellulose, starch or guar. Chitosan and chitosan derivative compounds are suitable. Cationic polysaccharides have the general formula (III):

$$G\text{-}O\text{—}B\text{—}N^+R^1R^2R^3X^{(-)} \qquad (III),$$

wherein G is a anhydroglucose residue, for example starch or cellulose anhydroglucose;

B is a divalent group, for example, an alkylene, an oxyalkylene, a polyoxyalkylene or hydroxyalkylene;

$R^1$, $R^2$ and $R^3$ are each, independently of each other, alkyl, aryl, alkylaryl, arylalkyl, alkoxyalkyl or alkoxyaryl with up to 18 carbon atoms respectively, wherein the total number of carbon atoms in $R^1$, $R^2$ and $R^3$ is at most 20; X is a common counter anion and is the same as in formula (I) and is preferably chloride. A cationic cellulose compound is marketed under the trade name Polymer JR of Amerchol and has the INCI name, polyquaternium-10. An additional cationic cellulose compound has the INCI name, polyquaternium-24, and is marketed by Amerchol under the trade name, Polymer LM-200. A suitable cationic guar derivative compound is marketed under the trade name JAGUAR® R and has the INCI name, guar hydroxypropyltrimonium chloride. Chitosan, chitosan salts and chitosan derivative compounds are especially preferred as cationactive materials. The chitosan used in the composition of the invention is partially or completely deacetylated. Chitin is an economical and plentiful natural raw material available in the shell resides of crustaceans. The molecular weights of chitosans can vary over a wide range, for example from 20,000 to 5,000,000 g/mol. A low molecular weight chitosan with a molecular weight of from 30,000 to 70,000 g/mol is suitable for example. For the purpose of the present invention the molecular weight preferably is above 100,000 g/mol, especially preferably form 200,000 to 700,000 g/mol. The deacetylation degree amounts to from 10 to 99%, especially preferably form 60 to 99%. A preferred chitosan salt is chitosonium pyrrolidone carboxylate, which for example is marketed under the trade name Kytamer PC of Amerchol, USA. The chitosan obtained has a molecular weight of about 200,000 to 300,000 g/mol and is deacetylated up to 70 to 85%. Quaternary, alkylated or hydroxyalkylated derivative chitosan compounds, for example, the hydroxyethyl chitosan, hydroxypropyl chitosan or hydroxybutyl chitosan, are suitable in the compositions according to the invention. The chitosans or chitosan derivative compounds should be present in neutralized or partially neutralized form when used in the compositions of the invention. The neutralization degree for the chitosan or the chitosan derivative compounds is preferably at least 50%, especially preferably between 70 and 100%, relative to the number of free base groups. In principle, all cosmetically compatible inorganic or organic acids may be used as neutralization agent, for example formic acid, tartaric acid, malic acid, lactic acid, citric acid, pyrrolidone carboxylic acid, hydrochloric acid, among other. Pyrrolidone carboxylic acid and the lactic acid are especially preferred as neutralization agents.

Pigments

In a preferred embodiment of the invention the hair wax product also includes at least one pigment. This pigment can be a colored pigment, which imparts a color effect to the product mass or the hair or it can be a luster effect pigment, which imparts a luster effect to the hair or the product mass. The color and luster effects on the hair are preferably temporary, i.e. they are maintained until the next hair washing and can be removed by washing the hair again with conventional shampoos. The pigments are present in the product mass in undissolved form. They can be contained in an amount of 0.01 to 25 percent by weight, especially preferably from 5 to 15 percent by weight.

The pigments are preferably micro-pigments, not nano-pigments. The preferred particle size amounts to from 1 to 200 μm, especially from 3 to 150 μm, especially preferably from 10 to 100 μm.

The pigments are practically insoluble coloring agents and can be inorganic or organic. Also inorganic-organic mixed pigments may be used. Inorganic pigments are preferable. The advantage of the inorganic pigments is their outstanding light-resistance, weather-resistance and temperature-resistance. The inorganic pigments can be of natural origin, for example chalk, ocher, umber, green earth, burnt siena or graphite. The pigments can be white pigments, such as titanium dioxide or zinc oxide; black pigments, such as iron oxide black; fancy or multi-colored pigments, such as ultramarine or iron oxide red; lustrous pigments, metal effect pigments, pearlescent pigments as well as fluorescene or phosphorescent pigments. Preferably at least one pigment is a colored, non-white pigment. Metal oxides, metal hydroxides and metal oxide hydrates, mixed phase pigments, sulfur-containing silicates, metal sulfides, complex metallo-cyanides, metal sulfates, metal chromates and metal molybdates and metals themselves (bronze pigments) are suitable. In particular, titanium dioxide (C.I. 77891), black iron oxide (C.I. 77499), yellow iron oxide (C.I. 77492), red and brown iron oxide (C.I. 77491), manganese violet (C.I. 77742), ultramarine (sodium aluminum sulfosilicate, C.I. 77007, Pigment Blue 29), chromium oxide hydrate (C.I. 77289), Iron Blue (Ferric ferrocyanide, C.I. 77510) and carmine (cochineal), are all suitable pigments.

Pigments based on mica and/or isinglass, which are coated with a metal oxide or metal oxychloride, such as titanium dioxide or bismuth oxychloride and if necessary other color-imparting materials, such as iron oxides, iron blue, ultramarine, carmine, etc, whose colors can be modified by changing the thickness of the coating, are especially preferred. Pigments of this sort are marketed, for example, under the trademark, Rona®, Colorona®, Dichrona® and Timiron® by the firm, Merck, Germany.

Organic pigments are, for example, the natural pigments, Sepia, gamboge, charcoal, Kasseler brown, indigo, chlorophyl and other plant pigments. Synthetic organic pigments include, for example, azo pigments, anthrquinoid pigments, indigoid pigments, dioxazine, quinacridone, phthalocyanine isoindolinone pigments, perylene pigments, perinone pigments, metal complex pigments, alkali blue pigments and diketopyrrolopyrrole pigments.

The hair wax product according to the invention can also contain dissolved colored substances or dyestuffs instead or in addition to pigments.

The hair wax compound according to the invention is preferably substantially water-free, i.e. it contains either no water or only a little water up to a maximum of 10 percent by weight, preferably less than five percent by weight.

Additional suitable hydrophobic, silicone-free soft waxy materials are used in amounts of e.g. 0.1 to 10 percent by weight. The solidification point of these soft waxy materials is in a range of about 25° C. to under 40° C., e.g. semisolid paraffins, especially products with the INCI name petrolatum, e.g. VASELINE®. These substances are semisolid mixture of hydrocarbons obtained from petrolatum.

Optional Additives

In addition to the above-described ingredients the composition according to the invention can also contain the following cosmetic additive ingredients:

solvents, such as univalent or polyvalent $C_1$- to $C_4$-alcohols, such as ethanol, isopropanol, glycerol or glycols in an amount of up to 15 percent by weight, preferably from 0.1 to 8 percent by weight;

dissolved cosmetic dyestuffs in an amount of up to 6 percent by weight, preferably from 0.1 to 4 percent by weight;

perfumes and fragrances in an amount of up to 2 percent by weight, preferably from 0.01 to 1 percent by weight or 0.2 to 0.5 percent by weight;

preservatives in an amount of up to 1 percent by weight, preferably from 0.01 to 0.5 percent by weight, especially p-hydroxybenzoic acid ester, benzoic acid, salicylic acid, sorbic acid, mandelic acid, polyhexamethylene biguanidine hydrochloride or isothazolinone derivative compounds;

hair care additives, such as betaine, panthenol, menthol, vitamins or similar substances in an amount of up to 5 percent by weight, preferably from 0.01 to 4 percent by weight or 0.1 to 0.5 percent by weight;

light-protective substances, UV filters, etc., in an amount of up to 5 percent by weight, preferably from 0.01 to 4 percent by weight.

Preferred Embodiment

A preferred embodiment of the hair wax product contains:

(A) 10 to 40% by weight of at least one silicone-free wax, which is an animal wax, a vegetable wax, a mineral wax, a synthetic wax, a microcrystalline wax, a macrocrystalline wax, a paraffin wax, ozokerite, a montan wax, a Fischer-Tropsch wax, a polyolefin wax, beeswax, lanolin, lanolin alcohol, candelilla wax, caranauba wax, Japan wax, a hardened fat, a fatty acid ester and/or a fatty acid glyceride;

(B) 20 to 80% by weight of at least one silicone compound that is liquid at 25° C., which comprises a linear polydimethylsiloxane, a cyclic polydimethylsiloxane, a hydroxysubstituted polydimethylsiloxane, an amino-substituted silicone and/or a siloxane substituted with aromatic groups;

(C) 5 to 40% by weight of at least one silicone wax with a melting point in a range of from 20 to 45° C., which comprises at least one alkylmethyl-dimethylsiloxane with an alkyl group containing at least eight carbon atoms;

(D) 0.1 to 30% by weight of at least one emulsifier;

(E) 0 to 15% by weight of at least one hair-fixing polymer; and (F) 0 to 10% by weight water.

Manufacturing Method

The hair wax products according to the invention could be made by melting the solid wax ingredients and mixing them with the remaining non-volatile ingredients. Subsequently the resulting mixture is cooled and shortly prior to solidification the volatile additive ingredients are added and mixed with it. The still fluid mass is then filled in the desired container, e.g. a plastic dish, prior to solidification.

Application Method

The use of the solid wax composition for treating hair is also part of the present invention. Also a method of treating hair is part of the present invention, in which hair is put in a hair style and the hair wax product according to the invention is prepared and applied to the hair.

Preferably the hair wax product is applied to dry hair. An amount, which can vary depending on the length of the hair, e.g. from approximately pea-size to approximately hazelnut size, is removed with the fingers. The wax is rubbed on the surface of the hand and is melted or at least greatly softened by the heat of the hand and by shear forces during rubbing. The wax is worked into the hair in a softened or more or less liquid state and the hair is set in the desired hairstyle. Also separated or individual hair strands can be treated in order to accentuate them. The wax hardens in the hair and the hairstyle formed obtains stability, luster, texture and hold.

The hair wax product according to the invention permits individual hairstyle formation and the targeted treatment of individual hair strands because of its waxy consistency and its cohesive properties. The product mass is easily distributed on the hair. The treated hair is characterized by an outstanding luster and by a high shape stability of the hairstyle set up. The hair is not excessively loaded and the product mass is easily washed. The hair wax product is characterized by reduced stickiness in comparison to commercial wax products for treating hair.

The following examples illustrate the subject matter of the invention in more detail without limitation of the appended claims.

EXAMPLES

Example 1

| | |
|---|---|
| 20 g | Hydrocarbon wax (ozokerite) |
| 48 g | Silicone oil (dimethylpolysiloxane, phenyltrimethicone, Dimethiconol) |
| 15 g | alkyl-modified silicone wax with melting point at about 30° C. (stearyl dimethicone) |
| q.s. | perfume |

Example 2

| | |
|---|---|
| 20 g | Hydrocarbon wax (ceresin) |
| 48 g | Silicone oil (dimethylpolysiloxane, phenyltrimethicone, Dimethiconol) |
| 15 g | alkyl-modified silicone wax with melting point at about 30° C. (stearyl dimethicone) |
| 16 g | emulsifier |
| q.s. | perfume |

Example 3

| Ingredients | A | B |
|---|---|---|
| Polydimethylsiloxane | 44 g | 44 g |
| Ceresin, liquefying point, 76-84° C. | 20 g | 35 g |
| Stearyl dimethicone | 15 g | — |
| Ceteareth-25 | 8 g | 8 g |
| Oleth-3 | 5 g | 5 g |
| Phenyltrimethicone | 3 g | 3 g |
| PPG-1-PEG-9 Lauryl glycol ether | 3 g | 3 g |
| Dimethiconol | 1.8 g | 1.8 g |

The ingredients of the compositions are melted at elevated temperatures, mixed with each other, filled in a plastic cup and allowed to cool.

The application properties of the above-described exemplary composition A according to the invention is compared with comparative composition B, which was not according to the invention, by sensory observation by feel. Hairs, which were treated with composition A according to the invention, have significantly less stickiness, than hairs treated with the comparative composition B.

The compositions according to the invention are characterized by good distributability, good workability into the hair, good washability, good structure and luster for hair treated with them, an anti-frizz effect, a natural hold of the hair, a smooth feel of the hair, a fashionable look to hair locks and satisfactory accenting of individual hair strands.

The disclosure in German Patent Application P10 2004 004 155.5 of Jan. 28, 2005 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in hair wax products containing silicone wax, silicone-free wax and oils, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

We claim:

1. A solid hair wax product for treating or setting up a human hair-do or hair style, said solid hair wax product containing of:
    at least one silicone-free wax;
    at least one hydrophobic oil which is liquid at 25° C. and is a liquid silicone compound;
    at least one silicone wax with a melting point in a range of from 20° C. to 45° C.;
    optionally from 0.1 to 8 percent by weight of a univalent $C_1$- to $C_4$-alcohol;
    optionally from 0.1 to 4 percent by weight of a dyestuff;
    up to 2 percent by weight of at least one member selected from the group consisting of perfumes and fragrances;
    up to 1 percent by weight of a preservative;
    up to 5 percent by weight of a betaine; and
    optionally from 0.01 to 4 percent by weight of at least one light-protective substance.

2. The solid hair wax product as defined in claim 1, wherein said at least one silicone-free wax has a solidification point above 40° C. and comprises an animal wax, a vegetable wax, a mineral wax, a synthetic wax, a microcrystalline wax, a macrocrystalline wax, a paraffin wax, ozokerite, a montan wax, a Fischer-Tropsch wax, a polyolefin wax, beeswax, lanolin, lanolin alcohol, candelilla wax, caranauba wax, Japan wax, a hardened fat, a fatty acid ester and/or a fatty acid glyceride.

3. The solid hair wax product as defined in claim 2, wherein said at least one silicone-free wax is a hydrocarbon wax.

4. The solid hair wax product as defined in claim 1, wherein said liquid silicone compound is selected from the group consisting of linear polydimethylsiloxanes, cyclic polydimethylsiloxanes, hydroxysubstituted polydimethylsiloxanes, amino-substituted silicones and siloxanes substituted with aromatic groups.

5. The solid hair wax product as defined in claim 1, wherein said at least one silicone wax has a melting point in a range of from 20° C. to 40° C. and is an alkyl-methyl-dimethylsiloxane, which contains an alkyl group with at least 8 carbon atoms.

6. The solid hair wax product as defined in claim 5, wherein said alkyl-methyl-dimethyl-siloxane is stearylmethyl-dimethylsiloxane.

7. A solid hair wax product for treating or setting up a human hair-do or hair style, said solid hair wax product consisting of:
    at least one silicone-free wax;
    at least one hydrophobic oil which is liquid at 25° C. and is a liquid silicone compound;
    at least one silicone wax with a melting point in a range of from 20° C. to 45° C.;
    optionally from 0.1 to 8 percent by weight of a univalent $C_1$- to $C_4$-alcohol;
    optionally from 0.1 to 4 percent by weight of a dyestuff;
    up to 2 percent by weight of at least one member selected from the group consisting of perfumes and fragrances;
    up to 1 percent by weight of a preservative;
    up to 5 percent by weight of a betaine;
    optionally from 0.01 to 4 percent by weight of at least one light-protective substance; and
    at least one emulsifier.

8. The solid hair wax product as defined in claim 7, wherein said at least one emulsifier is selected from the group consisting of ethoxylated fatty alcohols, ethoxylated fatty acids, ethoxylated fatty acid glycerides, ethoxylated alkylphenols, $C_{12}$- to $C_{22}$-fatty acid monoesters of addition products of 1 to 30 mol ethylene oxide with glycerol, $C_{12}$- to $C_{22}$-fatty acid diesters of addition products of 1 to 30 mol ethylene oxide with glycerol, addition products of 5 to 60 mol of ethylene oxide with castor oil or hydrogenated castor oil, monoesters of phosphoric acid with addition products of 2 to 30 mol of ethylene oxide with $C_8$- to $C_{22}$-fatty alcohols, diesters of phosphoric acid with addition products of 2 to 30 mol of ethylene oxide with $C_8$- to $C_{22}$-fatty alcohols, triesters of phosphoric acid with addition products of 2 to 30 mol of ethylene oxide with $C_8$- to $C_{22}$-fatty alcohols, fatty acid sugar esters, ethoxylated sorbitan fatty acid esters and polyglyceryl fatty acid esters.

9. A solid hair wax product for treating or setting up a human hair-do or hair style, said solid hair wax product consisting of:
    at least one silicone-free wax;
    at least one hydrophobic oil which is liquid at 25° C. and is a liquid silicone compound;
    at least one silicone wax with a melting point in a range of from 20° C. to 45° C.;
    optionally from 0.1 to 8 percent by weight of a univalent $C_1$- to $C_4$-alcohol;
    optionally from 0.1 to 4 percent by weight of a dyestuff;
    up to 2 percent by weight of at least one member selected from the group consisting of perfumes and fragrances;
    up to 1 percent by weight of a preservative;
    up to 5 percent by weight of a betaine;
    optionally from 0.01 to 4 percent by weight of at least one light-protective substance;
    at least one emulsifier; and
    at least one hair-fixing polymer.

10. The solid hair wax product as defined in claim 9, wherein said at least one hair-fixing polymer comprises
    at least one first polymer comprising at least one first monomer, wherein said at least one first monomer is selected from the group consisting of vinyl lactams, vinyl esters, vinyl alcohols, acrylamides, methacrylamides, alkylacrylamides, dialkylacrylamides, alkylmethacrylamides, dialkylmethacrylamides, dialkylaminoalkylmethacrylamides, dialkylaminoalkylacrylamides, alkylacrylates, alkylmethacrylates, propylene glycol and ethylene glycol;
    at least one second polymer comprising at least one second monomer, wherein said at least one second monomer is selected from the group consisting of acrylic acid, methacrylic acid, crotonic acid, maleic acid, maleic acid anhydride and monoesters of maleic acid;

at least one third polymer comprising at least one third monomer, wherein said at least one third monomer is selected from the group consisting of trialkylmethacryloxyalkylammonium compounds, trialkylacryloxyalkylammonium compounds, dialkyldiallylammonium compounds, alkylvinylimidazolium compounds, alkyvinylpyridinium compounds and alkylvinyl pyrrolidone compounds;

at least one fourth polymer comprising at least one fourth monomer having acid groups and at least one further monomer having basic amine groups; and/or at least one fifth polymer comprising at least one fifth monomer having both quaternary ammonium groups and acid groups or comprising at least one sixth monomer having said quaternary amine groups and at least one seventh monomer having said acid groups.

11. The solid hair wax product as defined in claim 7, having a solidification point greater than or equal to 30° C. and a needle penetration number in a range from 10 to 60 at 20° C.

12. A method for treating hair, said method comprising the steps of:

a) providing a solid hair wax product;
b) applying a portion of the solid hair wax product provided in step a) to the hair;
c) setting the hair in a hair-do or hair style; and
wherein said solid hair wax product consists of:
at least one silicone-free wax;
at least one hydrophobic oil which is liquid at 25° C. and is a liquid silicone compound;
at least one silicone wax with a melting point in a range of from 20° C. to 45° C.;
optionally from 0.1 to 8 percent by weight of a univalent $C_1$- to $C_4$-alcohol;
optionally from 0.1 to 4 percent by weight of a dyestuff;
up to 2 percent by weight of at least one member selected from the group consisting of perfumes and fragrances;
up to 1 percent by weight of a preservative;
up to 5 percent by weight of a betaine; and
optionally from 0.01 to 4 percent by weight of at least one light-protective substance.

13. The solid hair wax product as defined in claim 10, wherein said at least one first polymer is polyvinylpyrrolidone/vinyl acetate.

* * * * *